United States Patent
Langselius et al.

(10) Patent No.: US 9,532,568 B2
(45) Date of Patent: Jan. 3, 2017

(54) PRODUCT FOR MOLD PREVENTION AND TREATMENT

(71) Applicant: Miraculum, Inc., Austin, TX (US)

(72) Inventors: Britt Ann-Christine Langselius, Austin, TX (US); Freddy Kai Klaffmo, Arbrå (SE)

(73) Assignee: MIRACULUM, INC., Austin, TX (US)

( * ) Notice: Subject to any disclaimer, the term of this patent is extended or adjusted under 35 U.S.C. 154(b) by 0 days.

(21) Appl. No.: 14/339,888

(22) Filed: Jul. 24, 2014

(65) Prior Publication Data

US 2014/0336260 A1  Nov. 13, 2014

Related U.S. Application Data

(63) Continuation-in-part of application No. 14/161,677, filed on Jan. 22, 2014, now abandoned.

(60) Provisional application No. 61/755,053, filed on Jan. 22, 2013.

(51) Int. Cl.
| | | |
|---|---|---|
| A01N 37/02 | (2006.01) | |
| B05D 1/02 | (2006.01) | |
| B05D 1/28 | (2006.01) | |
| A01N 33/12 | (2006.01) | |
| A01N 37/36 | (2006.01) | |

(52) U.S. Cl.
CPC .............. *A01N 37/02* (2013.01); *A01N 33/12* (2013.01); *A01N 37/36* (2013.01); *B05D 1/02* (2013.01); *B05D 1/28* (2013.01)

(58) Field of Classification Search
None
See application file for complete search history.

(56) References Cited

U.S. PATENT DOCUMENTS

| | | |
|---|---|---|
| 4,648,904 A | 3/1987 | DePasquale et al. |
| 5,376,391 A | 12/1994 | Nisperos-Carriedo et al. |
| 6,287,585 B1 | 9/2001 | Johansen |
| 7,186,769 B2 | 3/2007 | Von Schmittou et al. |
| 8,575,085 B2 * | 11/2013 | Schwarz et al. ............... 510/384 |
| 2002/0119207 A1 | 8/2002 | Baker et al. |
| 2004/0219128 A1 | 11/2004 | Batdorf |
| 2005/0255251 A1 * | 11/2005 | Hodge et al. ................. 427/397 |
| 2007/0275101 A1 | 11/2007 | Lu et al. |
| 2008/0092937 A1 * | 4/2008 | Mitchell et al. .............. 136/200 |
| 2008/0148491 A1 | 6/2008 | van Buskirk et al. |
| 2009/0239994 A1 | 9/2009 | Tsuda et al. |
| 2011/0117035 A1 | 5/2011 | Jacquinot et al. |
| 2011/0182951 A1 | 7/2011 | Burger et al. |
| 2011/0240064 A1 | 10/2011 | Wales et al. |
| 2014/0031469 A1 * | 1/2014 | Tanimoto et al. ............ 524/238 |

FOREIGN PATENT DOCUMENTS

| | | | |
|---|---|---|---|
| WO | 2008074015 A1 | 6/2008 | |
| WO | WO 2008074015 A1 * | 6/2008 | |

OTHER PUBLICATIONS

Basic Mold Prevention (University of Florida, Institute of Food and Agricultural Sciences, accessed online Feb. 3, 2015).*
Ankner, "Cleaning and Killing Black Mold with Common, Non-Toxic, Household Products", Oct. 20, 2010 [retrieved on Jul. 30, 2014], Retrieved from the Internet: <URL: http://ezinearticles.com/cleaning-and-killing-black-mold-with-common,-non-toxic,-household-products&id=5237698>.
Dupont, "ZONYL 6700 Fabric Protector (Old Version)" Material Safety Data Sheet, Apr. 20, 2007 [retrieved on Feb. 3, 2015], Retrieved from the Internet: <URL: http://www.docstoc.com/docs/5901694/PEN_09004a2f800079eb>.

* cited by examiner

*Primary Examiner* — Robert A Wax
*Assistant Examiner* — Melissa Mercier
(74) *Attorney, Agent, or Firm* — Foley Hoag LLP

(57) ABSTRACT

A novel product for mold prevention and treatment is disclosed herein. The product comprises water, one or more anti-mold agents, one or more water-soluble fluoropolymers or other water-soluble polymers with similar properties, and one or more emulsifiers. In some embodiments, the product may further comprise one or more preservatives, one or more stabilizers, one or more binders, one or more fining agents, one or more firming agents, one or more thickeners, and/or one or more clarifying agents. The product may be non-toxic, biodegradable, effective for a long-period of time and against a wide variety of molds, and may also provide other features which render it safe for the environment as compared to other commonly used products in mold prevention and treatment.

5 Claims, No Drawings

PRODUCT FOR MOLD PREVENTION AND TREATMENT

CROSS-REFERENCE TO RELATED APPLICATIONS

This application is a continuation-in-part application of U.S. patent application Ser. No. 14/161,677, filed on Jan. 22, 2014, which claims priority to U.S. Provisional Patent Appl. No. 61/755,053, filed on Jan. 22, 2013, the disclosures of which are incorporated herein in their entireties by reference.

BACKGROUND

Field of the Invention

The present disclosure describes a novel product for mold prevention and treatment.

Description of the Related Art

Molds play an important role in the recycling of natural resources by breaking down dead organic matter. The presence of molds in the natural environment is thus extremely important. However, if molds are present indoors or grow on or inside structures, they can create various problems including a detrimental effect on health and structural integrity. Thus prevention of mold growth is an important challenge.

Molds reproduce by means of spores. These spores are invisible to the naked eye and readily disperse through outdoor and indoor air. Molds may begin growing indoors when mold spores land on wet surfaces. There are many types of molds, but all require moisture to grow.

Mold growth in homes and other buildings often causes suffering for individuals using the affected properties. Mold damage may also create large economic losses, as remediation of mold-affected structures often requires extensive effort. In some cases, it is impracticable to treat a structure and thus demolition is the only realistic option to resolve a mold problem.

For example, cleanup after a flood may involve thorough washing and disinfecting of the flooded area, including walls, floors, closets, shelves, and contents of the house or other affected structure. Common household cleaning products and disinfectants are often used for this task. Moreover, disinfectants and sanitizers may be applied to the ductwork for flooded heating and air conditioning systems. Commonly used disinfectants and sanitizers are often toxic to varying degrees, and use of such products for mold remediation may require extensive post-use ventilation to reduce the concentration of toxic substances in indoor air to safe and comfortable levels. Moreover, these toxic substances may be environmental pollutants. Many of the commonly used disinfectants and sanitizers also have a short effective lifespan for mold prevention or treatment, and therefore a new application may be required if mold or mold growth conditions reappear. This exacerbates the environmental harm caused.

Thus it is highly desirable to take preventative measures to inhibit mold growth under conditions that are otherwise highly suitable for mold growth. An ideal mold prevention agent will have at least the following properties: (1) it will not be toxic to humans, animals, and plants; (2) it will work quickly and efficiently; (3) it will remain effective for a long period of time; (4) it will be easy to use; (5) it will be biodegradable or at least not harmful to the environment; (6) it will not cause the release of toxic or corrosive substances if heated by fire or another source of heat, exposed to moisture or water from flooding, or otherwise affected under common types of natural or artificial disaster situations; (7) it will not migrate from the materials to which it is applied via evaporation or other forms of release; (8) it will not negatively affect the recyclability of materials to which it is applied; and (9) its production, processing, application, and disposal or recycling will not cause significant environmental harms. It may also be desirable to use a mold prevention agent with some or all of these properties for active mold control.

Recent efforts in the development of environmentally-friendly mold prevention and remediation agents have led to the development of various products including Foster Full Defense, MoldSTAT, Boral-20, and Vital Oxide. However, these products have varying degrees of environmental friendliness and non-toxicity, and are not known to be effective over a long period of time.

In addition, U.S. Patent Appl. Publ. Nos. 2007/0275101, 2004/0219128, and 2002/0119207, and PCT Patent Appl. Publ. No. WO 2008/074015 disclose various anti-mold compositions with varying degrees of environmental friendliness, non-toxicity, and long-term stability. However, these products are limited in their scope of use of particular types of applications.

Thus there remains a need for a safe, non-toxic agent for mold prevention and treatment That is effective over a long period of time and can be used in a wide variety of applications.

SUMMARY

A novel product for mold prevention and treatment is disclosed herein. The product comprises water, one or more anti-mold agents, one or more water-soluble fluoropolymers or other water-soluble polymers with similar properties, and one or more emulsifiers. In some embodiments, the product may further comprise one or more preservatives. In some embodiments, the product may further comprise one or more stabilizers. In some embodiments, the product may further comprise one or more binders. In some embodiments, the product may further comprise one or more fining agents. In some embodiments, the product may further comprise one or more firming agents. In some embodiments, the product may further comprise one or more thickeners. In some embodiments, the product may further comprise one or more clarifying agents. The product may be non-toxic, biodegradable, effective for a long-period of time and against a wide variety of molds, and may also provide other features which render it safe for the environment as compared to other commonly used products in mold prevention and treatment.

DETAILED DESCRIPTION OF THE PREFERRED EMBODIMENTS

The present disclosure describes a novel product for mold prevention and treatment. The product comprises water, one or more anti-mold agents, one or more water-soluble fluoropolymers or other water-soluble polymers with similar properties wherein the water-soluble fluoropolymers or other water-soluble polymers with similar properties are non-toxic in the amount used in the product, and one or more emulsifiers. In some embodiments, the product may further comprise one or more preservatives. In some embodiments, the product may further comprise one or more stabilizers. In some embodiments, the product may further comprise one or more binders. In some embodiments, the product may further comprise one or more fining agents. In some embodiments, the product may further comprise one or more firming agents. In some embodiments, the product may further comprise one or more thickeners. In some embodiments, the product may further comprise one or more clarifying agents.

The product may be applied to a material to render it mold resistant or to kill mold and/or mold spores. In preferred embodiments, the product may be applied to treat materials that are superficially bruised and materials that have been significantly affected by mold. In preferred embodiments, mold resistance resulting from treatment with the product will remain for a long period of time.

In preferred embodiments, the product adheres to a variety of materials. The product may be applied by spraying, brushing, or rolling it onto a surface, soaking a surface with a cloth soaked in the product, or by any other appropriate method.

In preferred embodiments, the product does not leave a readily visible residue on materials to which it has been applied. In preferred embodiments, the product penetrates slightly into the material to which it is applied. This allows treatment of mold that has penetrated the material, and provides enhanced mold inhibiting effects to inhibit future mold growth in treated materials.

In some embodiments, the product may be used to inhibit mold growth or kill mold and/or mold spores in materials such as wood, concrete, masonry, gypsum, and a variety of other materials that are frequently affected by mold. In preferred embodiments, the product is suitable for use indoors, including but not limited to use in attics, crawl spaces, basements, bathrooms, kitchens, and other mold-affected areas, and including but not limited to use on walls, floors, and other mold-affected surfaces and materials. In preferred embodiments, the treatment with the product does not negatively affect the treated material or surface.

In preferred embodiments, the product may be biodegradable in a natural environment. In preferred embodiments, the product may be non-toxic to humans, animals, and plants. Thus use of the product may not require protective gear that is generally required when applying hazardous chemical agents. In preferred embodiments, the product may be an aqueous solution or suspension, and may be free of sources of brominated heavy metals and other heavy metals. In preferred embodiments, the product may also be free of alkyd phosphates and bromides. In preferred embodiments, the product may provide excellent mold inhibiting or mold killing properties when distributed as a mist to minimize the amount of product used. A reduced amount of product needed may reduce storage and transportation needs for a mold treatment operation. In preferred embodiments, the product may be readily cleaned off equipment, tools, and materials to which it has been applied using a mild detergent and water. These features may render the product safe for the environment as compared to other commonly used mold prevention and treatment products.

In preferred embodiments, the product may be stable under ordinary conditions for long-term storage.

Use of the product may reduce the costs of treating mold-damaged structures and post-treatment remediation and restoration.

Product Description

The present disclosure describes a novel product for mold prevention and treatment. The product comprises water, one or more anti-mold agents, one or more water-soluble fluoropolymers or other water-soluble polymers with similar properties wherein the water-soluble fluoropolymers or other water-soluble polymers with similar properties are non-toxic in the amount used in the product, and one or more emulsifiers. In some embodiments, the product may further comprise one or more preservatives. In some embodiments, the product may further comprise one or more stabilizers. In some embodiments, the product may further comprise one or more binders. In some embodiments, the product may further comprise one or more fining agents. In some embodiments, the product may further comprise one or more firming agents. In some embodiments, the product may further comprise one or more thickeners. In some embodiments, the product may further comprise one or more clarifying agents.

In preferred embodiments, the anti-mold agent inhibits the growth of and kills mold. In some preferred embodiments, the anti-mold agent may also inhibit the growth of and kill bacteria. In preferred embodiments, the stabilizer retards decomposition of the product. In preferred embodiments, the binder prevents the product from separating into its components. In preferred embodiments, the fining agent stabilizes and promotes emulsification of the product. In preferred embodiments, the water-soluble fluoropolymers or other water-soluble polymers with similar properties reduce friction, enhance penetration of the product into the treated material, improve the weather-resistance of the product such that it is not readily washed away by rain or other weather events, and enhance the stability of the product. In highly preferred embodiments, the water-soluble fluoropolymers or other water-soluble polymers with similar properties enhance the stability of the product by retarding the decomposition of the anti-mold agent. In some embodiments, the preservative further retards decomposition of the product. In preferred embodiments, the clarifying agent removes particles from the product regardless of their polarity.

In preferred embodiments, the anti-mold agent comprises one or more ingredients selected from the group consisting of ethanol, benzyl chloride, benzalkonium chloride, quaternary ammonium compounds, citric acid, and dishwashing detergents. In some embodiments, the quaternary ammonium compounds may comprise one or more tetraalkyl ammonium chlorides. In some embodiments, the tetraalkyl ammonium chlorides may comprise didecyl dimethyl ammonium chloride. In preferred embodiments, the anti-mold agent comprises between 0.1% and 2.0% of the product. In more preferred embodiments, the anti-mold agent comprises between 0.2% and 1.5% of the product. In highly preferred embodiments, the anti-mold agent comprises between 0.6% and 1.0% of the product.

In preferred embodiments, the polymers comprise between 0.2% and 0.8% of the product.

In preferred embodiments, the emulsifier comprises one or more ingredients selected from the group consisting of low viscosity oils and surfactants. In preferred embodiments, the emulsifier comprises between 0.3% and 0.8% of the product.

In some embodiments, the product may further comprise one or more preservatives. In preferred embodiments, the preservative comprises one or more ingredients selected from the group consisting of benzalkonium chloride, benzoic acid and salts and esters, sorbic acid, pimaricin, sodium nitrate, and potassium nitrate. In preferred embodiments, the preservative comprises between 0.3% and 0.9% of the product.

In some embodiments, the product may further comprise one or more clarifying agents. In preferred embodiments, the clarifying agent comprises one or more ingredients selected from the group consisting of gelatin and kieselsol. In more preferred embodiments, the clarifying agent comprises between 0.05% and 0.15% of the product.

In some embodiments, the product may further comprise one or more stabilizers. preferred embodiments, the stabilizer comprises one or more ingredients selected from the group consisting of alginates, polyurethane, guar gum, and xanthan gum. In preferred embodiments, the stabilizer comprises between 0.45% and 1.15% of the product.

In some embodiments, the product may further comprise one or more binders. In preferred embodiments, the binder comprises one or more ingredients selected from the group consisting of polyurethane, polyesteral, and melamine. In preferred embodiments, the binder comprises between 0.2% and 1.0% of the product.

In some embodiments, the product may further comprise one or more fining agents. In preferred embodiments, the fining agent comprises bentonite. In preferred embodiments, the fining agent comprises between 0.15% and 1.0% of the product.

In some embodiments, the product may further comprise one or more firming agents. In preferred embodiments, the firming agent comprises calcium propionate. In preferred embodiments, the firming agent comprises between 0.2% and 0.8% of the product.

In some embodiments, the product may further comprise one or more thickeners. In preferred embodiments, the thickener comprises one or more ingredients selected from the group consisting of xanthan gum and pectins. In preferred embodiments, the thickener comprises between 0.15% and 0.75% of the product.

In preferred embodiments, the product is a transparent liquid. In some embodiments, the product has no odor. In preferred embodiments, the product has a boiling point between 95° C. and 105° C. at atmospheric pressure. In highly preferred embodiments, the product has a boiling point between 99° C. and 101° C. at atmospheric pressure. In preferred embodiments, the product has a freezing point between −6° C. and 4° C. at atmospheric pressure. In highly preferred embodiments, the product has a freezing point between −2° C. and 0° C. at atmospheric pressure. In preferred embodiments, the product has a pH between 7.3 and 8.0. In preferred embodiments, the product has a viscosity between 1.05 mPa·s and 1.35 mPa·s depending on its concentration. In preferred embodiments, the product has a density of between 1.0 g/mL and 1.2 g/mL.

In preferred embodiments, the product may be stable for long-term storage when stored in a sealed container at temperatures between its freezing point and 35° C.

EXAMPLES

The product may be prepared as a ready-to-use solution or a concentrate. In preferred embodiments, the ready-to-use solution comprises the following ingredients: water, an anti-mold agent, a sanitizer, a detergent, and a fluoropolymer.

In some preferred embodiments, the ready-to-use solution may preferably comprise ingredients in approximately the following ratios:
(1) 40 g citric acid
(2) 40 g sanitizer
(3) 60 g detergent
(4) 60 g fluoropolymer solution
(5) 9830 g water The ready-to-use solution may preferably comprise approximately 1-2% of the active mixture in water.

In some preferred embodiments, the concentrate may preferably comprise ingredients in approximately the following ratios:

(1) 40 g citric acid
(2) 40 g sanitizer
(3) 60 g detergent
(4) 60 g fluoropolymer solution
(5) 2872 g water The concentrate may be converted into the ready-to-use solution by diluting with water in a 2.25:1 ratio of water to concentrate.

Any effective anti-mold agent may be used. For the preparations below, the anti-mold agent was citric acid, obtained as citric acid monohydrate (2-hydroxy-1,2,3-propanetricarboxylic acid monohydrate), and a sanitizer.

Any ordinary sanitizer may be used. For the preparations below, the sanitizer used was a preservative, disinfectant sanitizer by Biosphere Innovation which comprises: water, dimethyl ammonium chloride (1-3%), didecyldimethyl ammonium chloride (1-3%), decyldimethyloctyl ammonium chloride (1-3%), and $C_8$-$C_{18}$-alkylbenzyldimethyl ammonium chloride (1-5%).

Any ordinary detergent may be used. For the preparations below, we used PowerPrep by Biosphere Innovation.

Any ordinary non-toxic water-soluble fluoropolymer or other water-soluble polymer with similar properties may be used. For the preparations below, a fluoropolymer product by Fiber ProTector Norge AS comprising 1-5% perfluoroalkyl copolymer, 5-10% acetic acid, and water was used.

Preparation of Ready-to-Use Solution:

The ready-to-use solution is prepared as described below. 8830 g of water is heated to approximately 10-20° C. in a suitable container. The water temperature should not be less than 5° C. or greater than 30° C. 60 g of the fluoropolymer product is then added to the water with electronic stirring and then the mixture is stirred until the fluoropolymer product dissolves completely. 60 g of the detergent is then added to the solution with electronic stirring and then the mixture is stirred until the detergent dissolves completely. 10 g of the citric acid is then added to the solution and stirred with an electronic stirrer until the citric acid dissolves completely. In a separate container, 1000 g of water is combined with 40 g of the sanitizer and stirred with an electronic stirrer until the sanitizer dissolves completely. The remaining 30 g of citric acid is then added to the solution comprising sanitizer and then stirred with an electronic stirrer until the citric acid dissolves completely. The solution comprising sanitizer and citric acid is then added to the solution comprising the fluoropolymer product, detergent, and citric acid, and the two solutions are mixed with an electronic stirrer to yield a uniform solution. The solution is then filtered and then poured into plastic containers of suitable size and each container is sealed with an airtight cap.

Excess stirring after components are dissolved may cause undesirable excessive drop in temperature of the solution. The sequence of addition of components minimizes undesired side reactions and promotes long-term stability of the product.

Preparation of Concentrate:

The concentrate is prepared according to a similar procedure as described for the ready-to-use solution. 1872 g of water is heated to approximately 10-20° C. in a suitable container. The water temperature should not be less than 5° C. or greater than 30° C. 60 g of the fluoropolymer product is then added to the water with electronic stirring and then the mixture is stirred until the fluoropolymer product dissolves completely. 60 g of the detergent is then added to the solution with electronic stirring and then the mixture is stirred until the detergent dissolves completely. 10 g of the citric acid is then added to the solution and stirred with an electronic stirrer until the citric acid dissolves completely. In a separate container, 1000 g of water is combined with 40 g of the sanitizer and stirred with an electronic stirrer until the sanitizer dissolves completely. The remaining 30 g of citric acid is then added to the solution comprising sanitizer and then stirred with an electronic stirrer until the citric acid dissolves completely. The solution comprising sanitizer and citric acid is then added to the solution comprising the fluoropolymer product, detergent, and citric acid and the two solutions are mixed with an electronic stirrer to yield a uniform solution. The solution is then filtered and then poured into plastic containers of suitable size and each container is sealed with an airtight cap.

Excess stirring after components are dissolved may cause undesirable excessive drop in temperature of the solution. The sequence of addition of components minimizes undesired side reactions and promotes long-term stability of the product.

The disclosure and examples above are intended as illustrative and are not intended to limit or otherwise restrict the invention. Numerous variations and modifications will become apparent to those skilled in the art upon full appreciation of the above disclosure. For example, one skilled in the art will understand that a variety of different formulations that rely on the same underlying principles used to generate the formulations disclosed above may effect the same results as the disclosed formulations. It is intended that the following claims be interpreted to embrace all such variations and modifications.

All references cited herein are expressly incorporated by reference.

What is claimed is:

1. A method of treating a material to render it mold resistant comprising: applying to the material a product comprising:
   water;
   a water-soluble perfluoroalkyl copolymer;
   citric acid; and
   a tetraalkyl ammonium chloride.

2. The method of claim 1, wherein one application of the product is sufficient to confer mold resistance on the material.

3. The method of claim 1, wherein the water-soluble perfluoroalkyl copolymer comprises approximately 0.006 to 0.03 percent of the product by weight.

4. The method of claim 1, wherein the citric acid comprises approximately 0.03 percent of the product by weight.

5. The method of claim 1, wherein the material comprises one or more materials selected from wood, concrete, masonry, or gypsum.

* * * * *